United States Patent [19]

Shiga et al.

[11] 4,151,165

[45] Apr. 24, 1979

[54] PROCESS FOR PREPARATION OF N,N'-DISUBSTITUTED-4,4'-BIPYRIDYLIUM SALT

[75] Inventors: Masaaki Shiga, Tokyo; Teruyuki Misumi; Takashi Tanaka, both of Kanagawa, all of Japan

[73] Assignee: Asahi Kasei Kogyo Kabushiki Kaisha, Osaka, Japan

[21] Appl. No.: 889,408

[22] Filed: Mar. 23, 1978

[30] Foreign Application Priority Data

Mar. 29, 1977 [JP] Japan .................................. 52/34037
Dec. 13, 1977 [JP] Japan ............................... 52/148852

[51] Int. Cl.² .......................................... C07D 213/22
[52] U.S. Cl. ..................................... 546/257; 546/258
[58] Field of Search ................................... 260/296 D

[56] References Cited

U.S. PATENT DOCUMENTS

| | | | |
|---|---|---|---|
| 3,696,113 | 10/1972 | Colchester et al. | 260/295 AM |
| 3,714,174 | 1/1973 | Colchester et al. | 260/295 AM |
| 3,716,546 | 2/1973 | Colchester | 260/295 AM |
| 3,864,352 | 2/1975 | Colchester et al. | 260/295 AM |

*Primary Examiner*—John D. Randolph
*Attorney, Agent, or Firm*—Armstrong, Nikaido, Marmelstein & Kubovcik

[57] ABSTRACT

A novel process for the preparation of an N,N'-disubstitued-4,4'-bipyridylium salt, characterized in that an N,N'-disubstitued tetrahydro-4,4'-bipyridyl corresponding to the desired salt is treated with at least one aromatic nitro compound in the presence of water. The process of the present invention is more advantageously effected further in the presence of a water-immiscible organic solvent. According to the present invention, the desired product can be obtained with high purity and in high yield.

11 Claims, No Drawings

PROCESS FOR PREPARATION OF N,N'-DISUBSTITUTED-4,4'-BIPYRIDYLIUM SALT

The present invention relates to a process for the preparation of a bisquaternary salt of 4,4'-bipyridyl, i.e., and N,N'-disubstituted-4,4'-bipyridylium salt. More particularly, the present invention relates to a process for preparing an N,N'-disubstituted-4,4'-bipyridylium salt by oxidation with an aromatic nitro compound in the presence of water.

It is well-known that bisquaternary salts of 4,4'-bipyridyls have a potent herbicidal activity and particularly, N,N'-dimethyl-4,4'-bipyridylium salts have already been practically used as herbicides.

These compounds are ordinarily prepared from 4,4'-bipyridyls according to the quaternization reaction. They can also be synthesized by oxidizing the corresponding N,N'-disubstituted tetrahydro-4,4'-bipyridyls. Oxidizing agents that can be used for this oxidation reaction are disclosed in, for example, Japanese Patent Publications Nos. 16060/1966, 4985/1970, 31181/1970, 11818/1971 and 11230/1972, and U.S. Pat. Nos. 3,644,383, 3,706,752 and 3,696,113.

For example, in Japanese Patent Publication No. 16060/1966, it is disclosed that, among organic compounds acting as a hydrogen acceptor and having an oxidation-reduction potential higher than $-1.48$ V, benzoquinones, nitroalkanes, unsaturated carboxylic acids and the like are preferred as the oxidizing agents.

We made investigation into these known oxidizing agents and we found that when an N,N'-disubstituted tetrahydro-4,4'-bipyridyl is oxidized with an organic oxidizing agent such as a benzoquinone or an unsaturated carboxylic acid, the obtained N,N'-disubstituted-4,4'-bipyridylium salt is generally insoluble in organic solvents and comes to be deposited in the form of solid as the reaction proceeds. The anion of the obtained salt is, in general, an anionic product formed due to the reduction of the oxidizing agent. Thus, the process in which such an organic oxidizing agent is employed inevitably requires an additional step for recovering the product and the oxidizing agent, which renders the process more disadvantageous or unsuitable from an industrial point of view.

The inventors of the present invention have made extensive and intensive studies on various oxidizing agents for N,N'-disubstituted tetrahydro-4,4'-bipyridyls, especially, aromatic nitro compounds which are easily available as industrial chemicals at reasonable costs. In general, aromatic nitro compounds are poor in oxidizing ability for N,N'-disubstituted tetrahydro-4,4'-bipyridyls and useless for the purpose when they are used alone. As a result of the studies, they have surprisingly found that the aromatic nitro compounds unexpectedly exert a remarkably high oxidizing ability when used in the presence of water. The present invention has been achieved based on such novel finding.

It is therefore an object of the present invention to provide an excellent process for preparing an N,N'-disubstituted-4,4-bipyridylium salt in high yield.

It is another object of the present invention to provide a process of the character described, which can be easily conducted at low cost.

The foregoing and other objects, features and advantages of the present invention will be apparent to those skilled in the art from the following detailed description and appended claims.

According to the present invention, there is provided a process for the preparation of an N,N'-disubstituted-4,4'-bipyridylium salt, which comprises treating an N,N'-disubstituted tetrahydro-4,4'-bipyridyl with at least one aromatic nitro compound in the presence of water.

As the N,N'-disubstituted tetrahydro-4,4'-bipyridyl to be used as the starting material in the process of the present invention, there can be mentioned N,N'-di(C$_1$–C$_5$)-alkyltetrahydro-4,4'-bipyridyls such as N,N'-dimethyltetrahydro-4,4'-bipyridyl, N,N'-diethyltetrahydro-4,4'-bipyridyl, N,N'-di-n-and -iso-propyltetrahydro-4,4'-bipyridyls, N,N'-di-n-, -iso-, -sec- and -tert-butyltetrahydro-4,4'-bipyridyls, N,N'-di-n-, -iso-, -sec-, -active- and -tert-amyltetrahydro-4,4'-bipyridyls. Of these starting materials, N,N'-dimethyltetrahydro-4,4'-bipyridyl is most preferred. The process of the present invention is also applicable to the case where an N,N'-di(C$_1$–C$_5$)alkyltetrahydro-4,4'-bipyridyl having such a substituent bonded to the pyridine nucleus as a halogen atom, a C$_1$–C$_5$ alkyl group, a hydroxyl group or an amino group is used as a starting material.

N,N'-Dialkyltetrahydro-4,4'-bipyridyls such as mentioned above can be prepared according to known methods. For example, they can be prepared by reducing an N-alkylpyridinium salt such as N-methylpyridinium chloride with sodium amalgam or by electrolytically reducing such an N-alkylpyridinium salt.

As the aromatic nitro compound to be used as the reactant or oxidizing agent in the process of the present invention, there can be mentioned, for example, nitrobenzene, nitrotoluenes, nitrochlorobenzenes, dinitrobenzenes, nitroanilines, nitrobromobenzenes, nitronitrosobenzenes, nitrobiphenyls, nitrophenetoles, sodium nitrophenoxides, nitrobenzyl alcohols, nitrobenzyl chlorides, nitrobenzamides, sodium nitrobenzenesulfonates, nitrobenzonitriles, nitroxylenes, nitronaphthalenes, nitrotoluidines, nitrothioanisoles, nitrostyrenes, nitrostilbenes, nitrodiphenylamines, nitro-N-dimethylanilines, nitrocymenes, sodium nitrobenzoates, nitroanthraquinones, nitroanisoles, nitroacetanilides and a mixture thereof. The aromatic nitro compound may be used in an amount of 1 to 100 moles, preferably 2 to 10 moles per mole of the N,N'-disubstituted tetrahydro-4,4'-bipyridyl. In case the amount of the employed aromatic nitro compound is less than 1 mole, the reaction time is prolonged and the yield is lowered. In case the amount of the aromatic nitro compound is larger than 100 moles, various consecutive side reactions are caused and the selectivity of the reaction is lowered.

In the reaction according to the process of the present invention, the presence of water is indispensable. When water is not present, the reaction rate is drastically reduced and the yield of the intended compound is very low.

In general, better results are obtained as the amount of water is increased. Water may ordinarily be used in an amount of 100 to 3,000 moles, preferably 1,000 to 2,000 moles, per mole of the N,N'-disubstituted tetrahydro-4,4'-bipyridyl. The larger the amount of water, the higher the yield and the shorter the reaction time. The upper limit of the amount of water is not particularly critical, but from the economical viewpoint or from the viewpoint of the equipment cost, it is preferred that water be used in an amount smaller than 3,000 moles per mole of the N,N'-disubstituted tetrahydro-4,4'-bipyridyl. When the amount of water exceeds about 3,000 moles per mole of the N,N'-disubstituted tetrahydro- 4,4'-bipyridyl, no substantial increase of the yield of the intended compound can be expected any more. When the amount of water is smaller than 100 moles per mole of the N,N'-disubstituted tetrahydro-4,4'-bipyridyl, various disadvantages are caused. For example, both the reaction rate and the yield of the intended compound are reduced.

It is preferred that water to be used in the present invention be degassed water. The presence of a minute amount of oxygen dissolved in water will not cause so fatal decrease in yield but tends to change the color of the reaction mixture to blackish brown and to reduce the selectivity of the reaction while promoting the occurrence of undesirable side reactions such as decomposition into monomers and formation of by-products of unknown composition. This leads to difficulty in the subsequent separation or purification of the intended product. Accordingly, it is preferred to remove dissolved oxygen from water as much as possible.

The reaction is ordinarily carried out at room temperature and atmospheric pressure substantially in the absence of oxygen. The reaction temperature and pressure, however, are not critical in the present invention. The reaction may be carried out at a temperature below the decomposition point of the starting material and it is generally effected at a temperature of 0° C. to 50° C., preferably, 10° C. to 30° C. The reaction pressure may be changed in the range of from 1 to 100 atm. The reaction time may be varied according to other reaction conditions such as the reaction temperature and the amount of water employed, but in general, the reaction is conducted for 30 minutes to 5 hours. The reaction atmosphere is rather critical. If the reaction is carried out in an atmosphere of air, the yield is drastically lowered, accompanied by formation of various unknown by-products which are difficult to separate, thus leading to unfavorable contamination therewith of the intended product.

In practicing the process of the present invention, the reaction may be effected without using an organic solvent as a reaction medium. In this case, it is noted that when an aromatic nitro compound of the liquid form, for example nitrobenzene, is used without agitation of the reaction system, the reaction system is caused to separate into the upper N,N'-dimethyltetrahydro-4,4'-bipyridyl layer, an intermediate aqueous layer and a lower nitrobenzene layer and hence the reaction is inhibited. In such case, with an appropriate agitation of the reaction system, it is possible to effect the reaction stably. On the other hand, when a solid aromatic nitro compound such as nitrochlorobenzene is employed or when the amount of an aromatic nitro compound is as small as nearly equimolar to the amount of the N,N'-disubstituted tetrahydro-4,4'-bipyridyl even if there is employed a liquid aromatic nitro compound such as nitrobenzene, solids of the unreacted aromatic nitro compound or a product formed by the reduction of the aromatic nitro compound are precipitated. The precipitate can be easily separated by filtration to obtain the filtrate containing the intended compound.

Alternatively, according to the process of the present invention, the reaction may be conducted in the presence of an organic solvent unreactive with the starting compound, the reactant and the resulting compound and having no bad influences on the intended reaction. By the use of such an organic solvent, the above-mentioned precipitation can advantageously be avoided so that such an additional step as the filtration may be omitted and the process can be easily conducted, and further, the intended reaction can proceed smoothly and stably. As the solvent, a water-immiscible organic solvent is preferred. When a water-immiscible organic solvent is used, the N,N'-disubstituted tetrahydro-4,4'-bipyridyl and the aromatic nitro compound are dissolved in the solvent and reaction products such as the N,N'-disubstituted-4,4-'bipyridylium salt and the N-substituted pyridinium salt are dissolved in water. As the water-immiscible organic solvent that may be suitably used in the process of the present invention, there can be mentioned, for example, saturated chain hydrocarbons such as n-pentane, n-hexane, n-heptane, n-octane, n-nonane, n-decane, isopentane, isohexane, isoheptane, isooctane, petroleum ether, gasoline and kerosene; cycloaliphatic hydrocarbons such as cyclopentane, cyclohexane, methylcyclohexane, cyclohexene and 1,3-cyclohexadiene; aromatic hydrocarbons such as benzene, toluene, xylenes, ethylbenzene, propylbenzene, methylethylbenzenes, styrene, cumene, hemimellitene, pseudocumene and mesitylene; halogenated aromatic compounds such as chlorobenzene, dichlorobenzenes, chlorotoluenes, bromobenzene and fluorobenzene; aromatic amines such as aniline, N-methylaniline, N-ethylaniline, dimethylanilines, diethylanilines, toluidines and chloroanilines; aromatic cyano compounds such as benzonitrile; ethers such as diethyl ester, diisopropyl ether, di-n-butyl ether, di-n-hexyl ether, methyl phenyl ether, ethyl phenyl ether, ethyl benzyl ether, furan and 2-methylfuran; water-immiscible alcohols having 4 or more carbon atoms such as butyl alcohols, amyl alcohols, heptanols and hexanols; and amines such as triethylamine and triamylamines. They may be used alone or in mixture. Other water-immiscible organic solvents, as far as they are unreactive with any of the starting material, the reactant and the resulting reaction product in the reaction system, can be used in the present invention. Of these organic solvents, aromatic hydrocarbons such as toluene, xylenes and ethylbenzene, halogenated aromatic compounds such as chlorobenzene, and saturated chain hydrocarbons such as n-hexane and isooctane are preferred. The term "water-immiscible" as used herein is defined to mean that a solvent is insoluble or even if soluble it is soluble in water only at a concentration as low as 10% by weight or less.

When such water-immiscible organic solvent is used, it is preferred that the amount of the water-immiscible solvent be in the range of 5 to 50% by volume based on the amount of water. If the water-immiscible organic solvent is used in an amount of within this range, the majority of the water-immiscible solvent is dispersed in water in the form of oil drops.

The manner of introducing an organic solvent into the reaction system is variable. Illustratively stated, one mode is that the starting N,N'-disubstituted tetrahydro4,4'-bipyridyl and the aromatic nitro compound are first charged and then the organic solvent is added. However, it is convenient that the organic solvent is introduced in the form of a solution in which the starting bipyridyl is dissolved in the organic solvent, because the starting bipyridyl can advantageously be obtained in the form of such a solution through the process of electrolytic dimerization of the N-substituted pyridinium salt. Alternatively, there may be adopted a further mode that the aromatic nitro compound or both the aromatic nitro compound and the starting bipyridyl are dissolved in the organic solvent and the resulting solution is introduced.

Also, when there is employed a water-immiscible organic solvent in the reaction of the process of the present invention, the agitation is advantageously conducted to attain the optimum dispersion state of the reaction system so that there can be obtained a good reaction performance such as yield, selectivity, reaction time, etc.

The reaction in the process of the present invention can be generally carried out in a batch type reaction vessel equipped with an agitator, but there can be used a continuous type reaction vessel or a tubular reaction vessel.

In practicing the process of the present invention, as mentioned before, the agitation is advantageously conducted. In case the reaction vessel equipped with an agitator is used, the optimum dispersion state can be realized when the agitator is rotated at 50 to 1,000 r.p.m., more preferably 100 to 700 r.p.m. In case the tubular reaction vessel is employed, the optimum dispersion state is attained by such an agitation that the Reynolds number is in the range of $10^3$ to $10^5$.

The reaction in the process of the present invention will now be described in detail referring to a specific embodiment in which a toluene solution containing N,N'-dimethyltetrahydro4,4'-bipyridyl at a concentration of 0.5 millimole/g is oxidized with nitrobenzene to form N,N'-dimethyl-4,4'-bipyridylium salt. The anion of the formed salt is not exactly known but it is believed to be a hydroxide ion.

In this embodiment, a preferred amount of nitrobenzene to be used is 2 to 5 moles per mole of N,N'-dimethyltetrahydro4,4'-bipyridyl, and an appropriate amount of water to be used is 1,500 to 2,000 moles per mole of the starting bipyridyl. When agitation is appropriately conducted in a batch type reaction vessel equipped with an agitator, the reaction is ordinarily completed within 1 hour. When the reaction is completed, the agitation is stopped and the reaction mixture is allowed to stand still, whereby the reaction mixture is separated into the organic phase and the aqueous phase. Unreacted nitrobenzene and reduction products of nitrobenzene such as azoxybenzene and azobenzene are dissolved in the organic phase, and if the reaction is completely achieved, the organic phase is transparent and light yellow. When the reaction is not completely effected, the organic phase has a deep blue color inherent of an unidentified intermediate product from N,N'-dimethyltetrahydro-4,4'-bipyridyl. (The original color of the organic phase before reaction is transparent and reddish brown.) Accordingly, completion of the reaction can be judged from the color of the organic phase. All the reaction products from N,N'-dimethyltetrahydro-4,4'-bipyridyl are easily soluble in water, and the aqueous phase is slightly turbid and has a reddish orange color.

Recovery of N,N'-dimethyl-4,4'-bipyridylium cation from the aqueous phase is accomplished by customary methods. For example, there can be adopted a method in which the bipyridylium cation is adsorbed on a cation exchange resin to separate it from the non-ionic residual mixture and said cation is recovered in the form of a salt by treating the cation exchange resin adsorbing the bipyridylium cation with an acid such as HCl, $H_2SO_4$, $H_3PO_4$ or acetic acid. The desired product may alternatively be recovered by adding a slightly excessive amount of amsonic acid (4,4'-diaminostilbene2,2'-disulfonic acid) to the aqueous reaction mixture to precipitate the desired product, followed by filtration, as described in U.S. Pat. No. 3,464,981. The recovery may also be made using chloroform according to the method as described in U.S. Pat. No. 3,506,677.

As the anion of an N,N'-disubstituted-4,4'-bipyridylium salt that may be useful as a herbicide, there can be mentioned, a chloride ion, a bromide ion, an iodide ion, a fluoride ion, a sulfate group, a benzenesulfonate group, a $C_1$–$C_{30}$ alkylsulfonate group, a trifluoromethanesulfonate group, a methosulfate group, a benzoate group, an acetate group, a citrate group, a lactate group, a fumarate group, a malate group, a maleate group, a salicylate group, a succinate group, a trichloroacetate group, a phosphate group, a cyanide group, a thiocyanate group, a nitrate group, a carbonate group, a fluorosilicate group, a tetrafluoroborate group and the like. A halide ion such as a chloride ion and a bromide ion, a sulfate group and a methosulfate group are especially preferred as the anion.

According to the process of the present invention, the intended bisquaternary salt can be obtained in high yield, and therefore, the process of the present invention is very advantageous from the industrial viewpoint.

The present invention will now be described in detail by reference to the following Examples, which should not be construed to limit the scope of the present invention.

EXAMPLE 1

N,N'-dimethyltetrahydro-4,4'-bipyridyl (DMTB) was prepared from N-methylpyridinium chloride by electrolytic dimerization and obtained in the form of a diethyl ether solution thereof. The so obtained diethyl ether solution was vacuum-distilled to obtain pure DMTB. As the pure DMTB tends to decompose immediately upon contact with oxygen in air, it was carefully handled in a nitrogen atmosphere. A 500 ml three-necked flask was sufficiently washed and dried and then completely filled with nitrogen gas. Into this flask were charged 200 ml of degassed water and 40 millimoles of nitrobenzene. 8 millimoles of DMTB was added, while stirring by rotating a magnetic stirrer having a length of 4 cm at 500 r.p.m., to the mixture charged in the flask, and the reaction was allowed to proceed at room temperature and atmospheric pressure in an atmosphere of nitrogen gas. The measurement of change, with the lapse of time, of pH showed that the pH changed from 6.8 to 12.7 one hour after the initiation of the reaction and it changed no more thereafter.

1 ml of the so obtained reaction mixture was sampled and diluted to 100 ml with pure water. About 1 mg of sodium dithionite ($Na_2S_2O_4$) was added to the diluted mixture and well mixed therewith. As a result, N,N'-dimethyl-4,4'-bipyridylium salt (DMB) was reduced to methylviologen cation radicals and the liquid assumed a clear blue color. Determination by absorption at a wavelength of 603 mµ with "Hitachi Double Beam Spectrophotometer of 200-10 Type (tradename of a ultraviolet spectrophotometer manufactured and sold by Hitachi Limited, Japan) showed that 54.8% of DMTB employed was converted to N,N'-dimethyl-4,4'-bipyridylium salt.

EXAMPLE 2

30.7 g of a toluene solution of DMTB obtained in substantially the same manner as in Example 1 and having a concentration of 0.344 millimole/g, 300 ml of degassed water and 6.4 g of nitrobenzene were charged into a 500 ml flask, and the reaction was allowed to proceed at room temperature and atmospheric pressure in a stream of nitrogen gas for 1 hour, while stirring by rotating a stirrer having a length of 4 cm at 300 r.p.m. The so obtained reaction mixture was allowed to stand still to be separated into an aqueous phase and an organic phase. The DMB dissolved in the aqueous phase was determined in substantially the same manner as in Example 1. The yield was 92.5% of the theoretical value.

EXAMPLE 3

10 g of a n-hexane solution of DMTB obtained in substantially the same manner as in Example 1 and having a concentration of 0.474 millimole/g, and 3.7 g of o-nitrochlorobenzene were allowed to react in the presence of 300 g of degassed water in substantially the same manner as in Example 1. The obtained DMB was determined in the same manner as in Example 1. The yield of the obtained DMB was 41.8% of the theoretical value.

EXAMPLE 4

There was prepared 20 g of a n-hexane solution containing DMTB at a concentration of 1.21 millimoles/g and nitrobenzene in an amount 5 times, in terms of mole, the amount of DMTB. The reaction was allowed to proceed, in a 500 ml flask, in the presence of degassed water in an amount 1,800 times, in terms of mole, the amount of DMTB in the stream of nitrogen gas at room temperature and atmospheric pressure for 1 hour. The yield of DMB was varied, as shown below, depending on the number of revolutions of the agitating blade employed.

| Number of revolutions, r.p.m. | 100 | 200 | 300 | 600 |
|---|---|---|---|---|
| Yield of DMB with respect to the theoretical value, % | 70.2 | 65.8 | 61.2 | 58.6 |

EXAMPLE 5

10 millimoles of DMTB dissolved in 20 ml of diethyl ether was added dropwise over 30 minutes to a mixture of 50 millimoles of nitrobenzene and 200 ml of water, while stirring by rotating a magnetic stirrer having a length of 4 cm at 500 r.p.m. in a 500 ml flask, to effect reaction. The reaction of the mixture was further allowed to proceed for additional 30 minutes. The reaction was conducted at room temperature and atmospheric pressure in the stream of nitrogen gas under the same stirring conditions as described above. The so obtained reaction mixture was heated to about 60° C. to remove the diethyl ether contained therein. 2 ml of the residual aqueous solution was sampled and the sample was diluted with pure water to have a 200-time volume. About 1 mg of sodium dithionite ($Na_2S_2O_4$) was then added to the thus diluted aqueous solution and the obtained product was converted to methylviologen cation radicals. The determination by absorption at a wavelength of 603 m$\mu$ with the same ultraviolet spectrophotometer as used in Example 1 showed that the yield was 78.6% of the theoretical value.

EXAMPLE 6

1 millimole of DMTB dissolved in 20 ml of n-hexane was added dropwise over 30 minutes to a mixture of 5 millimoles of nitrobenzene and 200 ml of water, while stirring, in a 300 ml flask, by rotating a magnetic stirrer having a length of 4 cm at 300 r.p.m., to effect reaction. The reaction of the mixture was further allowed to proceed for additional 30 minutes. The reaction was conducted at room temperature and atmospheric pressure in an atmosphere of nitrogen gas under the same stirring conditions as described above. The obtained reaction mixture was separated into an organic phase and an aqueous phase. 10 ml of the aqueous phase was sampled and diluted with pure water to have a 100-time volume. About 1 mg of sodium dithionite was then added to about 100 ml of the diluted sample and substantially the same colorimetric determination as in Example 5 was made. The yield was 82.5% of the theoretical value.

COMPARATIVE EXAMPLE 1

Substantially the same procedures as in Example 6 were repeated, but in the absence of water, while stirring by rotating a magnetic stirrer having a length of 4 cm at 500 r.p.m. and the reaction product was extracted with 200 ml of water. The N,N'-dimethyl-4,4'-bipyridylium salt dissolved in the aqueous phase was analyzed in the same manner as in Example 5. The yield was 5.4% of the theoretical value.

COMPARATIVE EXAMPLE 2

1 millimole of DMTB dissolved in 20 ml of n-hexane was added dropwise over 30 minutes to a mixture of 100 ml of a n-hexane solution containing 5 millimoles of p-benzoquinone and 100 ml of water, while stirring, in 300 ml flask, by rotating a magnetic stirrer having a length of 4 cm at 500 r.p.m., to effect reaction. The reaction of the mixture was further allowed to proceed for additional 30 minutes. The reaction was conducted at room temperature and atmospheric pressure in an atmosphere of nitrogen gas under the same stirring conditions as described above. The so obtained reaction product dissolved in the aqueous phase was analyzed in the same manner as in Example 5. The yield was 21.7% of the theoretical value.

COMPARATIVE EXAMPLE 3

20 ml of a n-hexane solution containing 1 millimole of DMTB was added dropwise over 30 minutes to a mixture of 5 ml of nitromethane and 100 ml of water, while stirring, in a 300 ml flask, by rotating a magnetic stirrer having a length of 4 cm at 500 r.p.m., to effect reaction. The reaction of the mixture was further allowed to proceed for additional 30 minutes. The reaction was conducted at room temperature and atmospheric pressure in an atmosphere of nitrogen gas under the same stirring conditions as described above. The reaction product was analyzed in substantially the same manner as in Example 5. The yield was 1.2% of the theoretical value.

EXAMPLE 7

100 g of a n-hexane solution containing DMTB at a concentration of 0.282 millimole/g, nitrobenzene in an amount 5.5 times, in terms of mole, the amount of said DMTB, degassed water in an amount 1,830 times, in terms of mole, the amount of said DMTB were charged into a 500 ml round flask. The reaction was conducted at room temperature and atmospheric pressure in an atmosphere of nitrogen gas. The stirrer made of a semicircular glass plate having a diameter of 4 cm was employed and rotated at 290 r.p.m. The results were varied depending on the reaction temperature as shown below in terms of yield of DMB with respect to the theoretical value.

| Reaction time | Reaction temperature | | |
|---|---|---|---|
| | 2° C. | 25° C. | 40° C. |
| 1 hr | 14.5% | 49.1% | 65.4% |
| 3 hrs | — | 66.4% | — |
| 4 hrs | 58.3% | — | 62.3% |
| 4.5 hrs | 65.2% | — | — |

EXAMPLE 8

A n-hexane solution containing DMTB at a concentration of 0.442 millimole/g was obtained from the process of electrolytic dimerization of N-methylpyridinium chloride. 20 g of the so obtained solution, 44.2 millimoles of nitrobenzene and a given amount of degassed water were charged in a 500 ml Erlenmeyer flask. The reaction was allowed to proceed at room temperature and atmospheric pressure for 1 hour in an atmosphere of nitrogen gas, while stirring by rotating a magnetic stirrer having a length of 4 cm at 300 r.p.m. The obtained reaction mixture was allowed to stand still to be separated into an aqueous phase and a n-hexane phase. The product dissolved in the aqueous phase was analyzed in the same manner as in Example 5. The obtained results are shown below together with the amount of N-methylpyridinium salt formed as a byproduct, which salt can advantageously be utilized for the preparation of DMTB (starting material of the process of the present invention) by electrolytic dimerization. The anion of N-methylpyridinium salt is not exactly known but it is believed to be a hydroxide ion.

| Amount of water, g | Yield of DMB, % | Amount of N-methylpyridinium salt, % | Total, % |
|---|---|---|---|
| 200 | 71.0 | 26.9 | 97.9 |
| 100 | 69.0 | 23.5 | 92.5 |
| 60 | 63.5 | 17.8 | 81.3 |
| 30 | 49.0 | 22.5 | 71.5 |
| 20 | 29.6 | 19.6 | 49.2 |
| 10 | 9.2 | 18.7 | 27.9 |

What is claimed is:

1. A process for the preparation of an N,N'-disubstituted-4,4'-bipyridylium salt, which consists essentially of treating an N,N'-disubstituted tetrahydro4,4'-bipyridyl with at least one aromatic nitro compound in the presence of water and substantially in the absence of oxygen, said water being employed in an amount of at least 100 moles per mole of the N,N'-disubstituted tetrahydro-4,4'-bipyridyl.

2. A process for the preparation of an N,N'-disubstituted-4,4'-bipyridylium salt according to claim 1, wherein said treatment is carried out in the presence of a water-immiscible organic solvent which is capable of dissolving therein the N,N'-disubstituted tetrahydro-4,4'-bipyridyl and the aromatic nitro compound and unreactive with the reactants.

3. A process for the preparation of an N,N'-disubstituted-4,4'-bipyridylium salt according to claim 2, wherein the water-immiscible organic solvent is a member selected from the group consisting of saturated chain hydrocarbons, cycloaliphatic hydrocarbons, aromatic hydrocarbons, halogenated aromatic compounds, aromatic amines, aromatic cyano compounds, ethers, water-immiscible alcohols having 4 or more carbon atoms, and amines.

4. A process for the preparation of an N,N'-disubstituted-4,4'-bipyridylium salt according to claim 3, wherein the water-immiscible organic solvent is a member selected from the group consisting of saturated chain hydrocarbons, cycloaliphatic hydrocarbons and aromatic hydrocarbons.

5. A process for the preparation of an N,N'-disubstituted-4,4'-bipyridylium salt according to claim 1, wherein the N,N'-disubstituted tetrahydro-4,4'-bipyridyl is an N,N'-straight-chain or branched dialkyltetrahydro-4,4'-bipyridyl having 1 to 5 carbon atoms in the alkyl moiety.

6. A process for the preparation of an N,N'-disubstituted-4,4'-bipyridylium salt according to claim 1, wherein said at least one aromatic nitro compound is a member selected from the group consisting of nitrobenzene, nitrotoluenes, nitrochlorobenzenes, dinitrobenzenes, nitroanilines, nitrobromobenzenes, nitronitrosobenzenes, nitrobiphenyls, nitrophenetoles, sodium nitrophenoxides, nitrobenzyl alcohols, nitrobenzyl chlorides, nitrobenzamides, sodium nitrobenzenesulfonates, nitrobenzonitriles, nitroxylenes, nitronaphthalenes, nitrotoluidines, nitrothioanisoles, nitrostyrenes, nitrostilbenes, nitrodiphenylamines, nitro-N-dimethylanilines, nitrocymenes, sodium nitrobenzoates, nitroanthraquinones, nitroanisoles, nitroacetanilides and mixtures thereof.

7. A process for the preparation of an N,N'-disubstituted-4,4'-bipyridylium salt according to claim 1, wherein the water is used in an amount of 100 to 3,000 moles per mole of the N,N'-disubstituted tetrahydro-4,4'-bipyridyl.

8. A process for the preparation of an N,N'-disubstituted-4,4'-bipyridylium salt according to claim 7, wherein water is used in an amount of 1,000 to 2,000 moles per mole of the N,N-disubstituted tetrahydro-4,4'-bipyridyl.

9. A process for the preparation of an N,N'-disubstituted-4,4'-bipyridylium salt according to claim 1, wherein the aromatic nitro compound is used in an amount of 1 to 100 moles per mole of the N,N'-disubstituted tetrahydro-4,4'-bipyridyl.

10. A process for the preparation of an N,N'-disubstituted-4,4'-bipyridylium salt according to claim 9, wherein the aromatic nitro compound is used in an amount of 2 to 10 moles per mole of the N,N'-disubstituted tetrahydro-4,4'-bipyridyl.

11. A process for the preparation of an N,N'-disubstituted-4,4'-bipyridylium salt according to claim 1, wherein the treatment is carried out at a temperature of 0° to 50° C. under a pressure of 1 to 100 atmospheres for 30 minutes to 5 hours.

* * * * *